United States Patent [19]

Chitwood

[11] Patent Number: 5,441,479
[45] Date of Patent: Aug. 15, 1995

[54] CERVICAL TRACTION DEVICE

[75] Inventor: Ralph Chitwood, Kalispell, Mont.

[73] Assignee: Glacier Cross, Inc., Whitefish, Mont.

[21] Appl. No.: 120,602

[22] Filed: Sep. 13, 1993

[51] Int. Cl.⁶ ............................................. A61F 5/00
[52] U.S. Cl. ........................................ 602/18; 602/13; 606/240; 5/636; 5/640; 5/644; 128/DIG. 20; 128/DIG. 23; 128/845; 128/870
[58] Field of Search ..................... 602/13, 17, 18; 128/845, 869–870, DIG. 20, DIG. 23; 5/622, 636, 637, 640, 644; 606/240, 241

[56] References Cited

U.S. PATENT DOCUMENTS

| | | | |
|---|---|---|---|
| 3,343,532 | 9/1967 | Zumaglini | 602/18 |
| 4,058,112 | 11/1977 | Johnson | 5/637 X |
| 4,508,109 | 4/1985 | Saunders . | |
| 4,543,947 | 10/1985 | Blaekstone | 602/18 |
| 4,617,691 | 10/1986 | Monti et al. | 128/DIG. 23 X |
| 4,805,603 | 2/1989 | Cumberland | 128/DIG. 20 X |
| 4,850,003 | 7/1989 | Huebeck et al. . | |
| 5,067,483 | 11/1991 | Freed . | |
| 5,243,722 | 9/1993 | Gusakov | 5/644 X |
| 5,382,226 | 1/1995 | Graham . | |

Primary Examiner—Linda C. M. Dvorak
Attorney, Agent, or Firm—Thomas R. Vigil

[57] ABSTRACT

The cervical traction device comprises: a body including a shoulder portion, a head portion and a bellows which extends substantially across the width and height of the body between and connected to the head portion and to the shoulder portion and acting against and between substantially the full inner end surface of the head portion and the full inner end surface of the shoulder portion. The bellows, the shoulder portion and the head portion have aligned U-shaped openings therein adapted to receive a patient's neck. A hand operated air pump is connected to the bellows for pumping air into the bellows and for relieving or pumping air out of the bellows.

28 Claims, 5 Drawing Sheets

CERVICAL TRACTION DEVICE

BACKGROUND OF THE INVENTION

1. Field of the Invention

The present invention relates to a cervical traction device which is positioned under the neck of a patient lying on a flat surface between the shoulders and the head and which has an inflatable bellows located between a shoulder portion and a head portion of the cervical traction device. A hand operated bulb type air pump with a manually operated air pressure relief valve is connected to the bellows for manually expanding and contracting the inflatable portion thereby to stretch the neck and release the stretching force on the neck.

2. Description of the Related Art Including Information Disclosed Under 37 CFR §1.97-1.99

Heretofore it has been proposed to provide a traction pillow and an inflatable cervical traction pillow.

Examples of such pillows are disclosed in the following two U.S. Patents:

| U.S. Pat. No. | Patentee |
| --- | --- |
| 4,832,007 | Davis, Jr. et al. |
| 4,805,603 | Cumberland |

In U.S. Pat. No. 4,832,007 to Davis, Jr. et al. there is disclosed a traction pillow and method for using same. The pillow is made of resilient material and has a generally rotatable portion (cervical roll) for supporting the cervical region of a user. The cervical pillow has cavities therein which enable a medical technician to collapse the pillow by pressing down on it while the patient's neck is resting on the pillow.

In the Cumberland U.S. Pat. No. 4,805,603 there is disclosed a cervical traction apparatus comprising a head/neck/shoulder support unit having a vertical slot in the region corresponding to the cervical area. The slot separates the unit into a first section and a second section. The upper surfaces of each of the sections is shaped to receive the head, neck and shoulders of a reclining person. An inflatable air sack is located within the unit between the first and second sections and a hand operated bulb type air pump is provided for pumping up the air sack.

As will be described in greater detail herein after the present invention provides a specially contoured shoulder portion and a specially contoured head portion which are contoured in a different manner than the contours of the traction pillow and cervical traction pillow of the Davis Jr., et al. and Cumberland patents referred to above. More specifically, an arcuate shoulder seating surface is provided which seats on and against the upper or center portion of each shoulder and over and against the front chest portion of each shoulder; and, the head portion has a U-shaped surface and a head receiving surface with a shoulder being formed on each side of the U at the junction of the U-shaped surface and the head receiving surface for engaging the patient's occipital bone to enable the cervical traction device to exert pressure on the head to exert traction on the neck. Furthermore, instead of an air sack, a bellows is provided which extends substantially completely across the transverse extent of the cervical traction device. Still further, a head strap is provided together with attachment structure for attaching the head strap over a patient's head to the head portion to firmly hold the patient's head to the head portion of the cervical traction device thereby, in conjunction with the shoulder acting against the occipital, enhancing the gripping or holding of the patient's head to the head portion.

SUMMARY OF THE INVENTION

According to the present invention there is provided a cervical traction device comprising: a body including a shoulder portion, a head portion and a bellows which extends substantially across the width and height of the body between and connected to the head portion and to the shoulder portion and acting against and between substantially the full inner end surface of the head portion and the full inner end surface of the shoulder portion. The bellows, the shoulder portion and the head portion having aligned U-shaped openings therein adapted to receive a patients neck. A hand operated air pump is connected to the bellows for pumping air into the bellows and for relieving or pumping air out of the bellows.

DESCRIPTION OF THE PREFERRED EMBODIMENT

Figure 1:
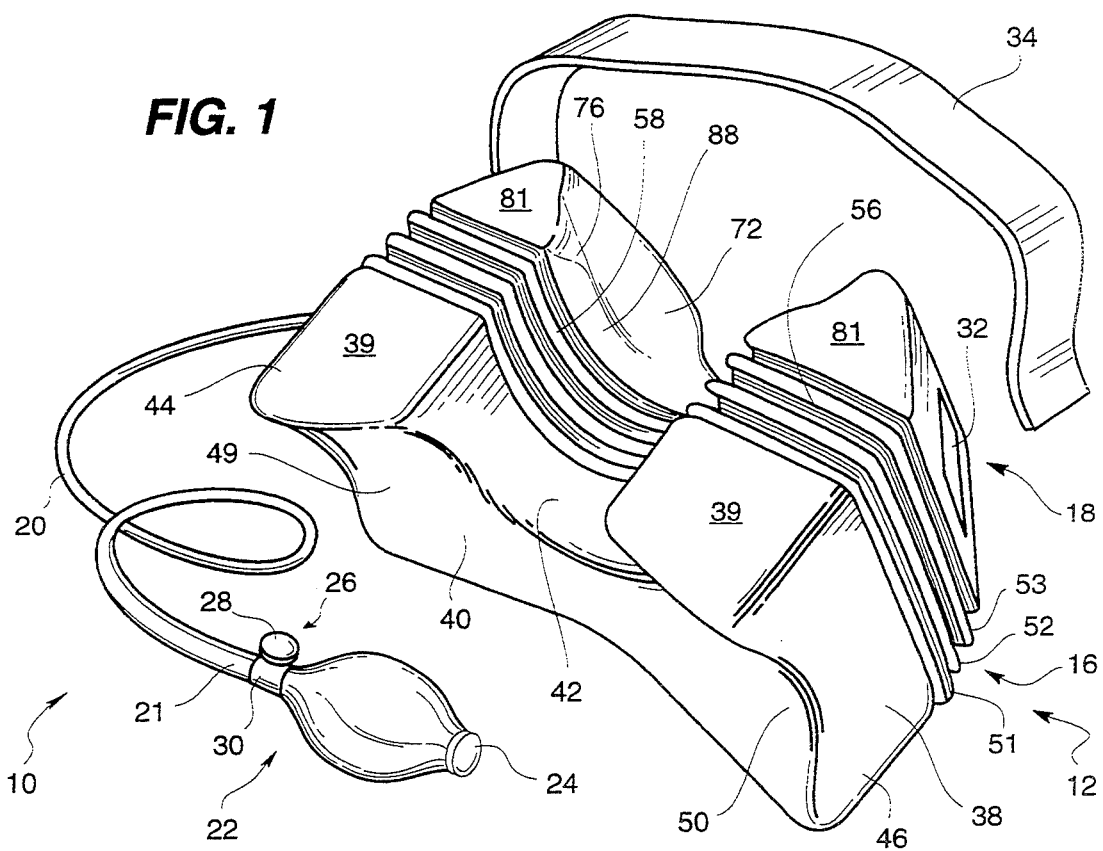
FIG. 1 is a perspective view of the cervical traction device constructed according to the teachings of the present invention.

Referring now to the drawings in greater detail there is illustrated in FIG. 1 a cervical traction device 10 constructed according to the teachings of the present invention. The device 10 includes a body 12 including a shoulder portion 14, a bellows 16, and a head portion 18.

The cervical traction device 10 further includes a tubing 20 connected to the bellows 16 and having, at an outer end 21 thereof, an air pump 22 in the form of compressible bulb 22 for pumping the bellows 16 with air. The compressible bulb 22 has, at its outer end, a one way inlet valve 24 which allows air to be sucked into the bulb 22, but does not allow air to flow out of the bulb 22 when it is compressed.

Adjacent to the bulb 22 and mounted on the tubing 20 is a relief valve 26 which comprises a knurled thumbscrew 28 mounted in a metal collar 30 fixed to the tubing 20. When the thumbscrew 28 is rotated into the collar 30, no air can escape from the bellows 16 and when the thumbscrew 28 is threaded outwardly, the valve 26 is opened to allow compressed air to escape from the bellows 16 through the tubing and out of the relief valve 26.

Figure 8:
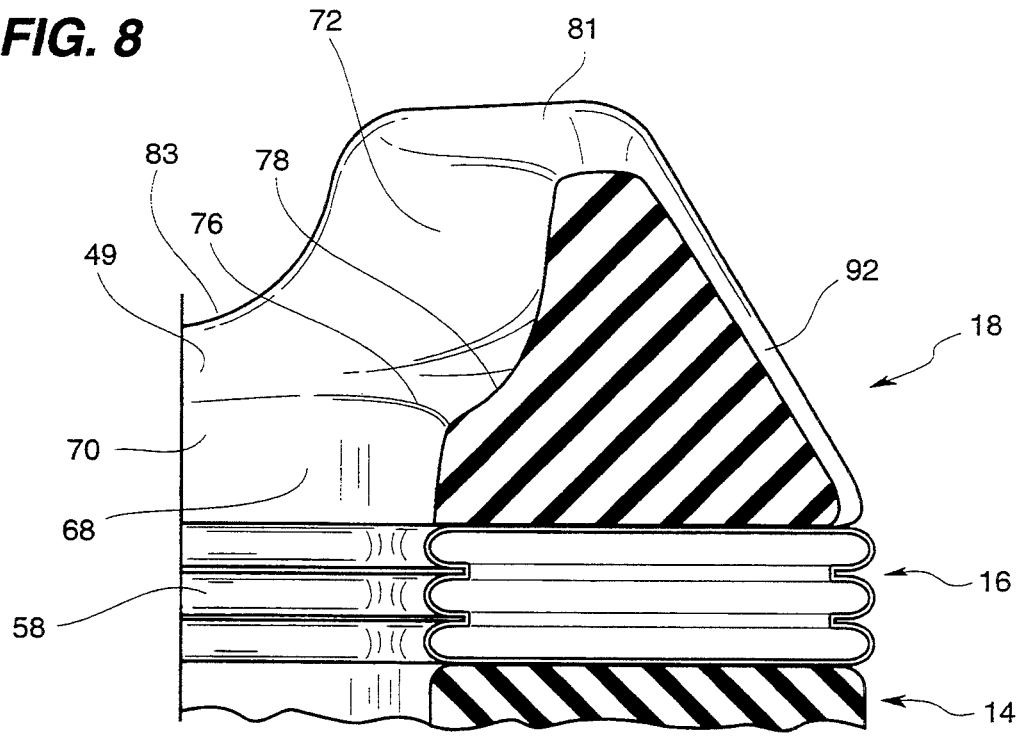
FIG. 8 is a sectional view through the head portion of the body of the cervical traction device and is taken along line 8—8 of FIG. 4.

In addition to the compressible bulb 22 and the tubing 20, the cervical traction device 10 includes, on either side of the head portion 18, a loop and hook type fastening structure 31,32 (FIG. 4) of the type sold under the trademark VELCRO ® and a head strap 34 which is adapted to be received over a patient's head. The strap 34 has on its inner surface 36 a fabric texture which is adapted to attach to the fastening structures 31 and 32. This readily can be seen in FIGS. 8 and 9 where there is shown a patient's head resting in the cervical traction device 10 with the shoulder portion 14 bearing against the patient's shoulders and the patient's head being received in the head portion 18 with the head strap 34 extending over the forehead and being connected to the fastening structures 31 and 32 on either side of the head portion 18.

As shown in FIGS. 2–7, the shoulder portion 14 (and the head portion 18 as well) is made of foam having sufficient elasticity to be comfortable to a patient and sufficient rigidity or hardness to establish traction, stretching or lift surfaces thereby to enable maximum traction forces to be created and is contoured to rest on the shoulders of a patient for enabling a counterstretch force to be created by the cervical traction device 10. In this respect it will be noted that the shoulder portion 14 has a bottom 36, opposite side walls 37 and 38, a top side 39, a contoured curved outer end surface 40 and an arcuate, semi-cylindrical or U-shaped surface 42 that extends downwardly from the top side 39 in the middle area thereof between two spaced apart block portions 44 and 46 of the shoulder portion 14. The shoulder portion 14 also has a generally flat inner end surface 48 which is fixed by adhesive or other means to one side 49 of the bellows 16.

Figure 2:
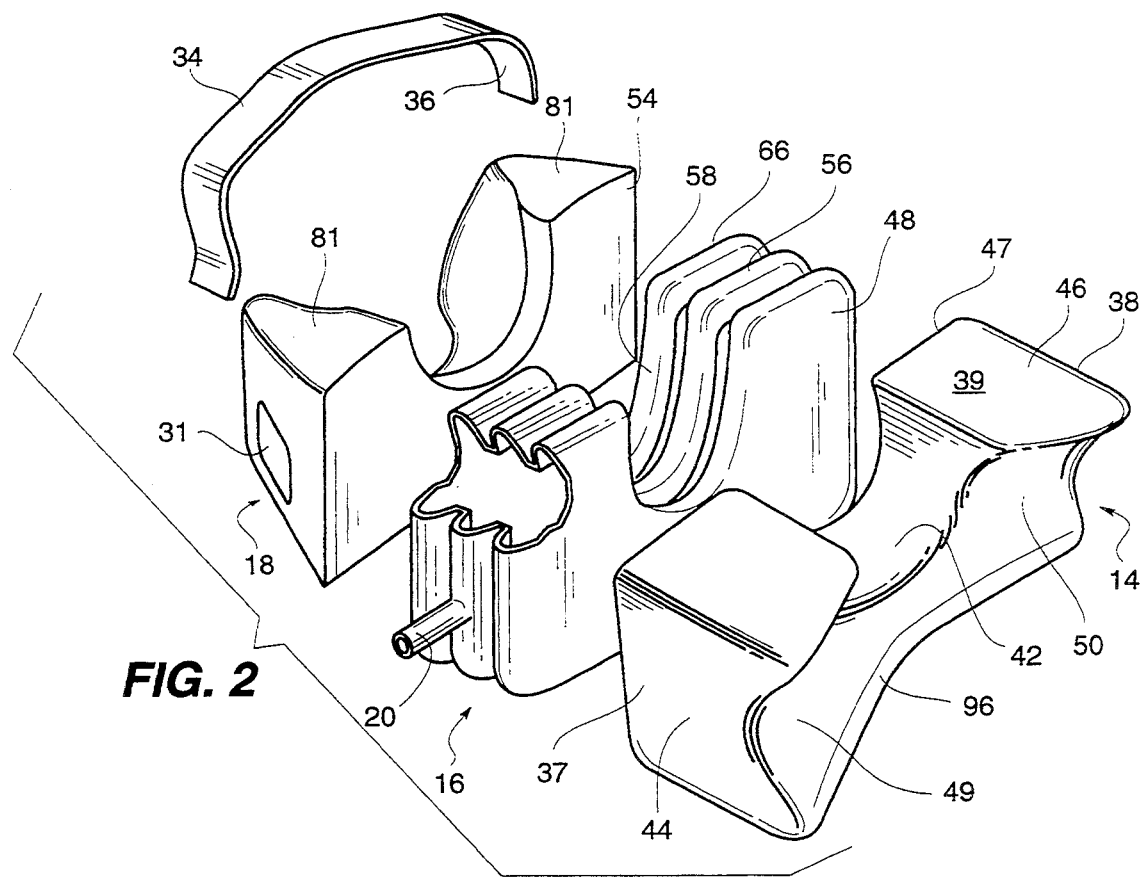
FIG. 2 is an exploded perspective view of the cervical traction device shown in FIG. 1 with portions cut away.

As best shown in FIGS. 1 and 2, the outer end surface 40 of the shoulder portion 14 inclines slightly inwardly towards the bellows 16 from each side wall 37 and 38 of the shoulder portion 14 to the middle of the shoulder portion 14 to accommodate the natural sloping of a patient's shoulders. Also from top to bottom, the contoured end surface 40 is curved inwardly and then outwardly to form arcuate surfaces 48 or 50 on the respective block portions 44 and 46 which are received over the natural contour of a patient's left and right shoulders. The extent of the U-shaped surface 42 from the inner end surface 48 toward the end surface 42 varies from approximately 1" in the middle area of the body 12 to approximately 2" at the top side 39.

The construction of the curved outer end surface 40 of the shoulder portion 14 enables the shoulder portion 14 to fit easily over the front and center portions of the shoulders of a patient to enable a better and more manageable stretch force to be applied against the patient's shoulders with a minimum of slippage.

The one piece bellows 16 is constructed with three undulations 51, 52 and 53 in the illustrated embodiment and is constructed and arranged to raise and support the cervical curve of a patient's neck during inflation. Also, to provide an even force along the width of the shoulder portion 14 adjacent the inner end surface 48, and most importantly, along the width of the head portion 18 adjacent an inner end surface 54 thereof, the bellows 16 is generally rectangular and extends substantially the full height and width of the body 12 of the device 10.

For this purpose the bellows 16 is generally rectangular and has a top side 56 and an arcuate, semi-circular or U-shaped surface 58 extending downwardly from the top side 56 generally aligned with the U-shaped surface 42 of the shoulder portion 14 to provide a nesting support for a patient's neck.

Most cervical injuries to patients involve the loss of the natural cervical curve forming a so called military neck or straight neck syndrome. This creates stress on the upper thoracic muscles, as these muscles are forced to hold the head upright. When the natural curve is in place, the head weight is distributed throughout the skeletal system. The body 12 of the cervical traction device 10 is constructed so that the patient's cervical curve is supported to relieve upper thoracic muscles from unnatural stress. The manner in which the shoulder portion 14 achieves this function at the center of the body 12 of the cervical traction device 10 is shown in FIG. 5 where the contoured surface 40 has a downwardly inclined portion 60 going up to a flat or slightly upwardly inclined surface portion 62 of the U-shaped surface 42.

The generally flat inner end surface 54 of the head portion 18 is secured to an opposite end surface 66 of the bellows 16 by adhesive or other suitable means. The head portion 18 then has a generally arcuate or semi-cylindrical U-shaped surface 68 having a portion 70 that inclines slightly downwardly at the center to fit the cervical curve of the patient's neck and has a head receiving surface 72 having a center portion 74 that curves downwardly for mating with the cervical curve.

The U-shaped surface 68 extends toward the outer end of the head portion a distance approximately ¾ of an inch to one inch and forms a shoulder 76 on opposite sides of the U-shaped curved surface 68 but not at the center of the U-shaped curved surface 68. This can be best seen in FIGS. 5, 6 and 7.

Figure 5:
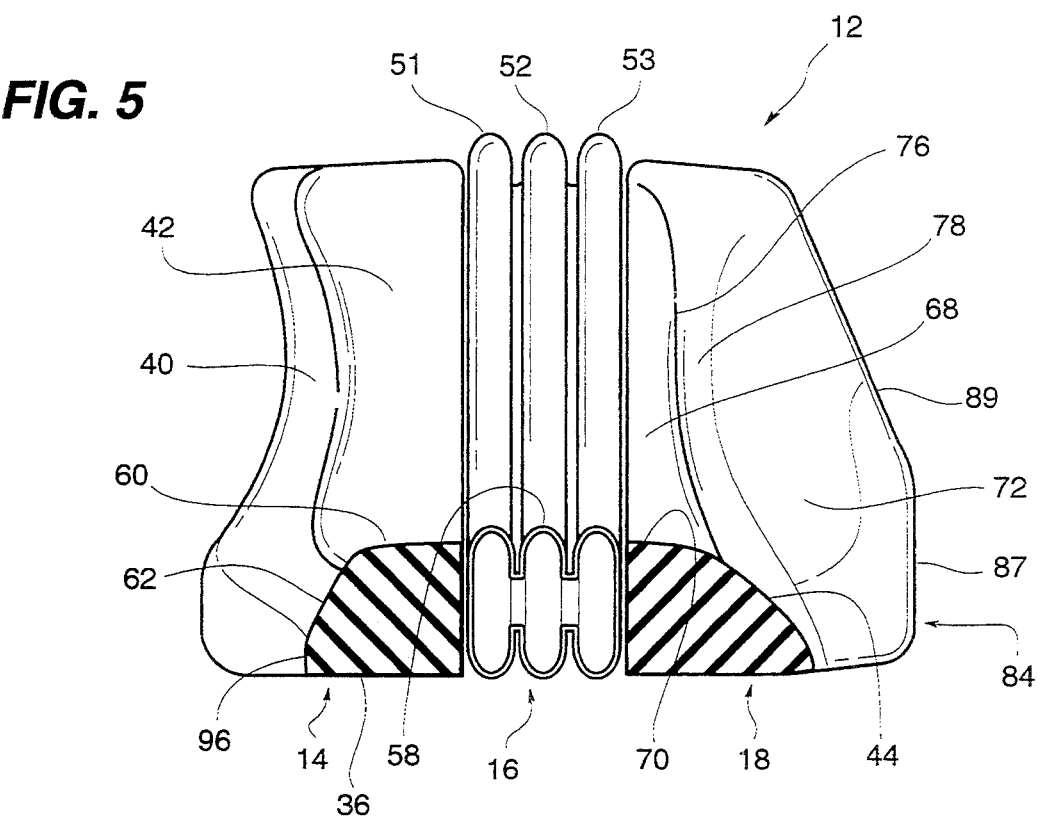
FIG. 5 is a sectional view through the body of the cervical traction device shown in FIG. 3 and is taken along line 5—5 of FIG. 3.

In FIG. 5 it will be seen that there is very little shoulder 76 with the U-shaped surface 68, 70 at the bottom of the U connecting with the surface portion 74 of the head receiving surface 72.

Figure 6:
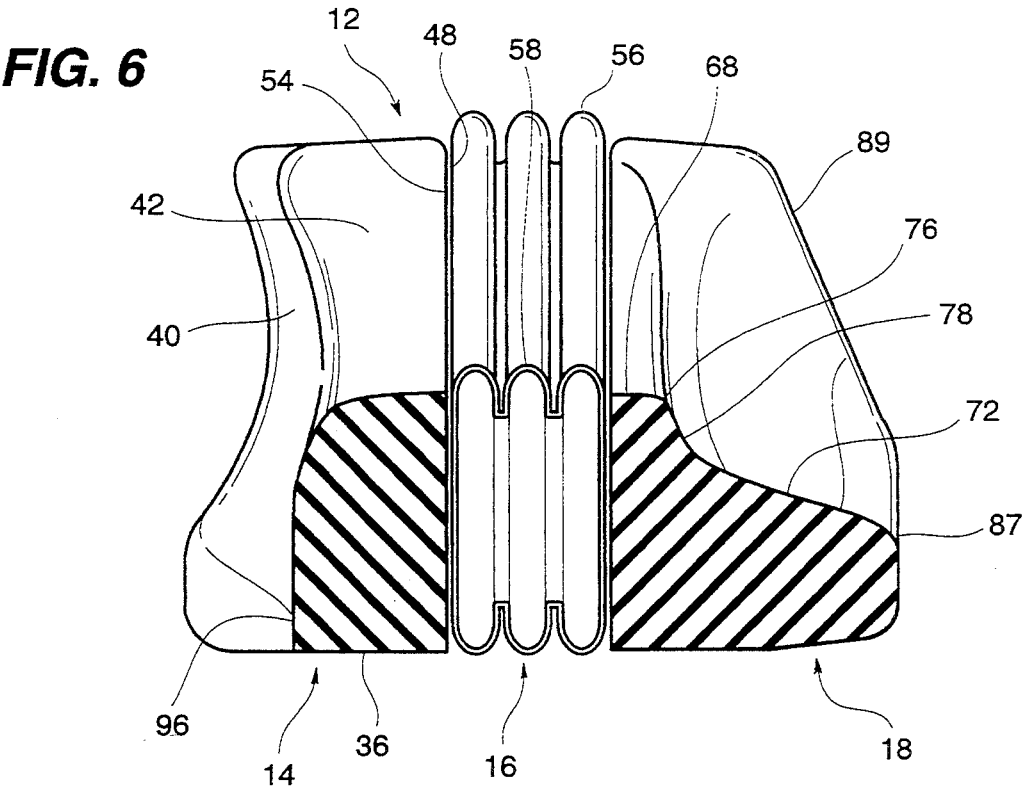
FIG. 6 is a sectional view through the body of the cervical traction device shown in FIG. 3 and is taken along line 6—6 of FIG. 3.

Then in FIG. 6 it will be seen that part way up either side of the U-shaped surface 68 the shoulder 76 is pronounced and is located at the junction between the U-shaped surface 68 and the specially contoured head receiving surface 72. The shoulder 76 at this location is adapted to bear against the occipital bone and defines in the head receiving surface an occipitalcervical pressure or lift surface 78 just outwardly of the shoulder 76.

This shoulder 76 and the adjacent pressure or lift surface 78 on the head receiving surface 72 enables the head portion 18 to apply pressure at the region of the occipital bone of a patient on each side of the neck. It is believed that this pressure on the occipital bone applied with the cervical traction device 10 of the present invention also can alleviate or relieve headache pain.

Figure 7:
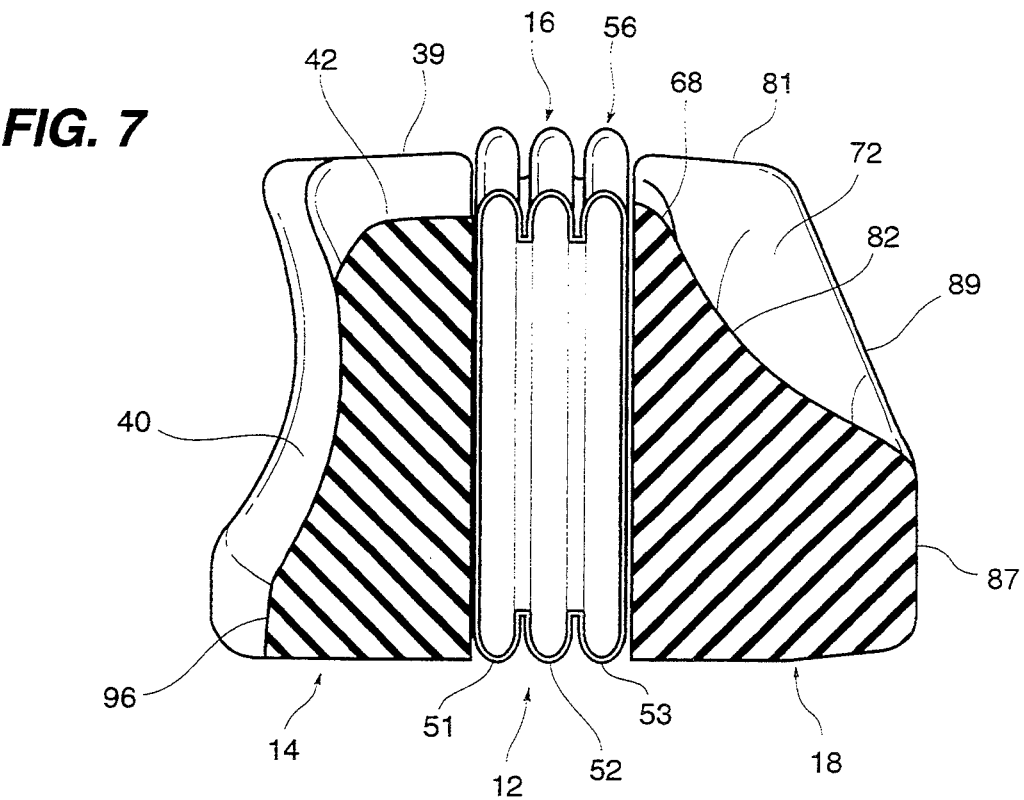
FIG. 7 is a sectional view through the body of the cervical traction device shown in FIG. 3 and is taken along line 7—7 of FIG. 3.

Looking now at FIGS. 5, 6 and 7 it will be appreciated that the body 12 has in the U-shaped openings and at the center of the U-shaped surfaces 42, 58, 68 the curved straight or inclined surface portions 62, 60, 42, 58, 70, and 74 for receiving the cervical curve of the neck (FIG. 5). Then as one moves to the left side or the right side of the U-shaped openings in the area of the U-shaped opening in the head portion 18, the head receiving surface 72 has the pronounced shoulder 76, the occipital bone receiving surface 78 and then a gentle sloping curving surface portion 80 (FIG. 6) for supporting the head above the occipital bone on each side of the head.

As shown in FIG. 7, near a top side 81 of the head portion 18, the U-shaped surface 68 slopes in a longitudinal direction downwardly and merges in or with a smooth downwardly extending curved surface portion 82 of the head receiving surface 72 which extends to an outer end 84 or 85 of the head portion 18 on each side of the head receiving surface 72.

The U-shaped opening 58 in the bellows 16 has, in the extended or inflated condition, a depth of between 3 and 4 inches and preferably 3 and ½ inches.

Figure 3:
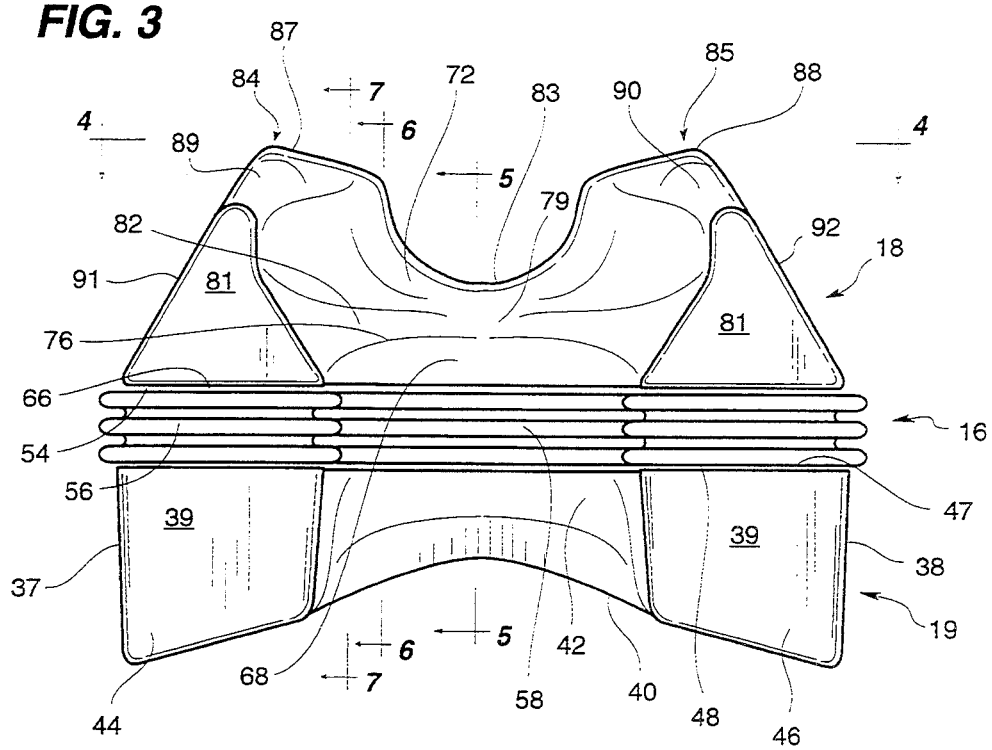
FIG. 3 is a top plan view of a body of the cervical traction device shown in FIG. 1.

Looking now at FIG. 3, it will be apparent that the specially contoured head receiving surface 72 extends downwardly to a bottom 86 in the central area of the head portion 18 such that the head portion has a U-shaped notch 87 at the bottom thereof where the head of a patient can then rest on a flat surface.

Then the ends 84, 85 of the head portion 18, on either side of the center thereof, has left and right end wall portions 87, 88 extending upwardly from the flat bottom 86 of the head portion 18 to sloping end wall portions 89, 90 which slope upwardly and inwardly toward the top side 81 of the head portion 18.

Also, as best shown in FIG. 3 left and right outer sides 91, 92 of the head portion 18 are inclined from the inner end surface 54 at the bellows 16 inwardly and outwardly to the upwardly and inwardly inclined end wall portions 89, 90. On each of these left and right outer sides 91, 92 there is provided the patches 31, 32 of hook and loop attaching material of the type sold under the trademark VELCRO ®. Each patch 31, 32 is located on the inclined side 91 or 92 adjacent the bottom 86.

Figure 4:
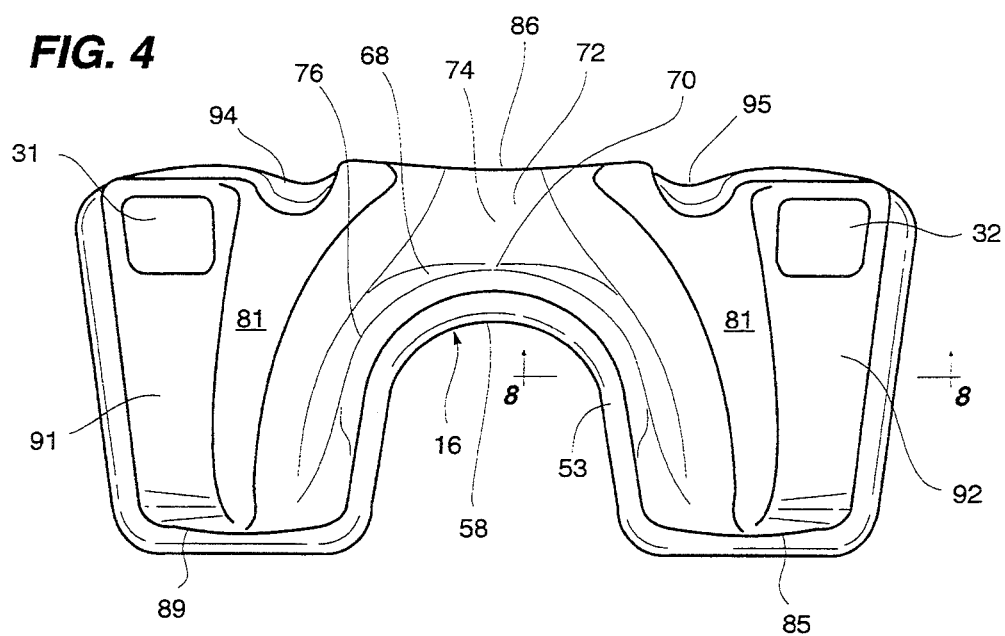
FIG. 4 is an end plan view of the body of the cervical traction device shown in FIG. 3 and is taken along line 4—4 of FIG. 3.

If desired, the bottom 86 of the head portion 18 can have an inclined slot or flute 94 or 95 therein on either side of the U-shaped notch 87 as shown in FIG. 4. Similarly the shoulder portion 14 can have two or four inclined slots or flutes on the bottom 36 thereof extending inwardly from a lower end wall 96 (which extends upwardly from the bottom 36 to the curved end portion 40) and downwardly to the bottom 36 on either side of the center of the body 12 of the cervical traction device 10.

Figure 9:
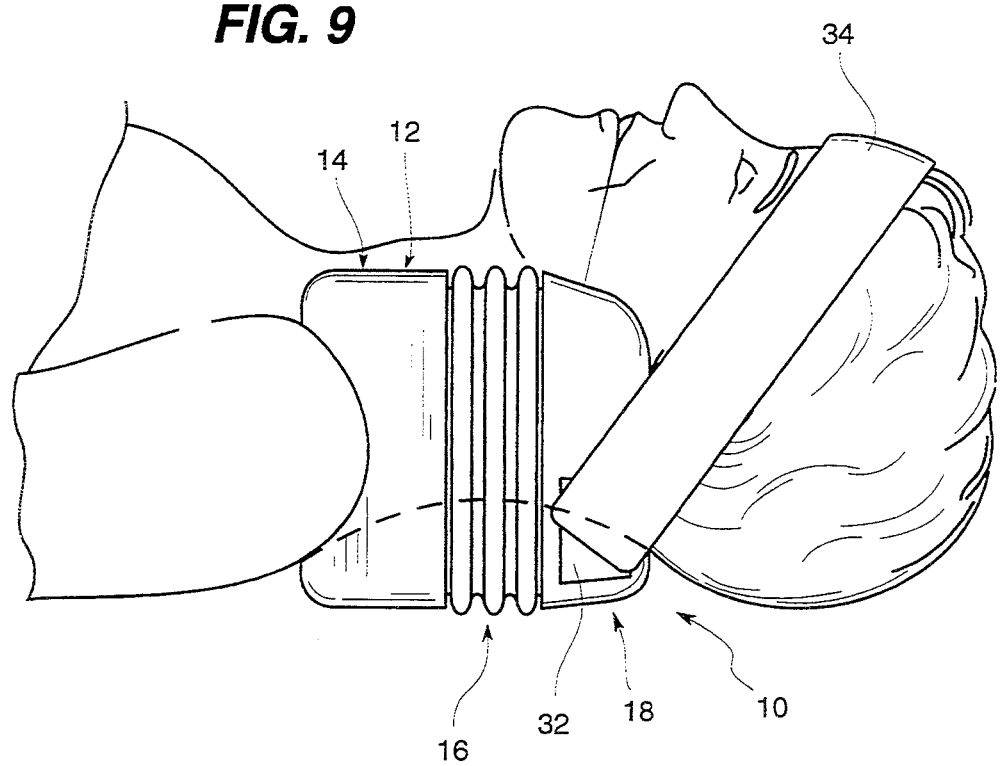
FIG. 9 is a side plan view of the cervical traction device with the neck of a patient resting therein with the device being in a deflated or non-extended condition.
Figure 10:
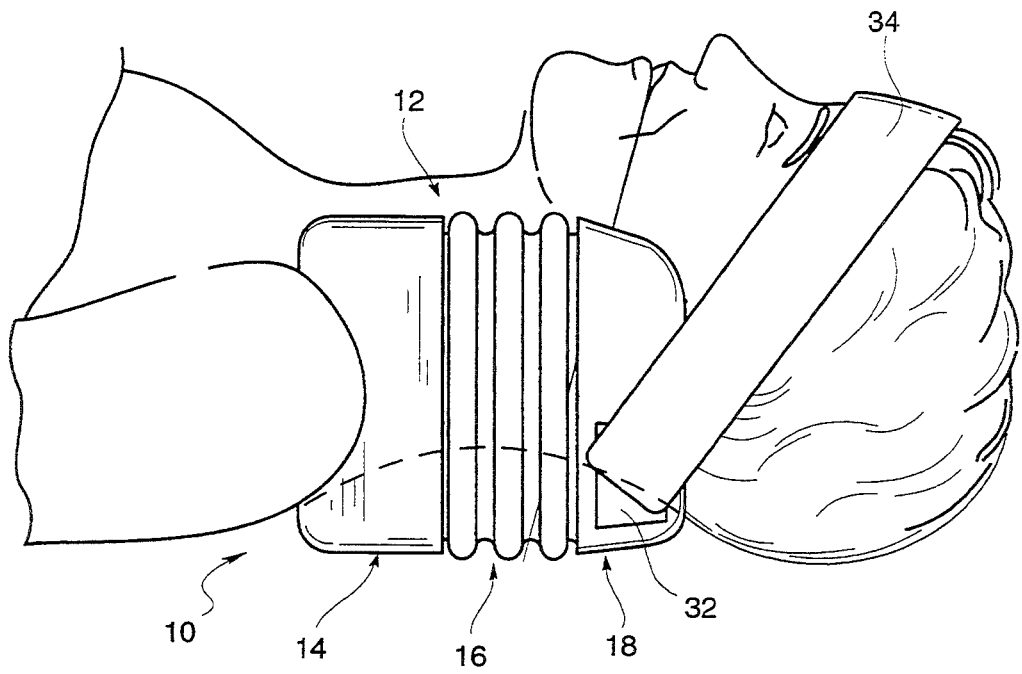
FIG. 10 is a side elevational view of a patient resting in the cervical traction device, similar to the view shown in FIG. 3, but showing the cervical traction device in an inflated or extended condition.

As best shown in FIGS. 1, 9 and 10 the head strap 34 has a fabric attachment structure 36 of the type sold under the trademark VELCRO ® on the inside 36 of the strap 34 which, at each end of the strap 34, is adapted to be received over a patient's forehead and secured to the patches 31, 32 to securely hold the patient's head to the head portion 18 of the body 12 of the cervical traction device 10 to achieve the greatest stretch or traction.

In the use of the cervical traction device 10 a patient will place the device 10 on a flat surface such as a floor or table and lay down on the floor or table with the cervical curve of the patient's neck received over the center of the U-shaped opening formed by the U-shaped opening, i.e., over surfaces or surface portions 62, 60, 42, 58, 72, 74, in the shoulder portion 14, the bellows 16 and the head portion 18. Then the patient, a doctor or other medical technician will place the strap 34 over the head of the patient and secure it firmly to the patches 31, 32. Next, the patient, a doctor or a medical technician will pump the hand-held bulb type air pump 22 to pump up the bellows 16 to create traction on the cervical area of the patient's neck supported by the surface portions 62, 60, 42, 58, 72, 74, in the shoulder portion 14, the bellows 16 and the head portion 18.

If desired an electrically operated air pump (not shown) can be connected to the tubing 20 in place of the bulb type hand-operated air pump 22. Such an electronic pump will include a timer for cycling the electrical pump through intermittent pump and relief cycles thereby to apply intermittent traction to the patient's neck for treating muscle spasm and herniated disk conditions of a patient. Intermittent traction is preferred for alleviating a patient's pain caused by muscle spasm or a herniated disk. In this modification, air can be pumped into or out of the bellows portion under the control of a timer having three different time cycles.

From the foregoing description, it will be apparent that the cervical traction device 10 of the present invention has a number of advantages, some of which have been described above and others of which are inherent in the invention.

Also from the foregoing description it will be apparent that modifications can be made to the cervical traction device 10 without departing from the teachings of the invention.

Accordingly the scope of the invention is only to be limited as necessitated by the accompanying claims.

I claim:

1. A cervical traction device comprising: a body including a shoulder portion, a head portion and a bellows which extends substantially across the width and height of said body between and connected to said head portion and to said shoulder portion and acting against and between substantially the full inner end surface of said head portion and the full inner end surface of said shoulder portion; said bellows, said shoulder portion and said head portion having aligned U-shaped openings therein adapted to receive a patient's neck; and, means, connected to said bellows, for pumping air into said bellows and for relieving or pumping air out of said bellows.

2. The cervical traction device of claim 1 wherein said shoulder portion has an outer end surface specially contoured to seat over the top center and front chest portions of the left and right shoulders of a patient and bear against said left and right shoulders when the bellows is inflated.

3. The cervical traction device of claim 2 wherein said shoulder portion has a top, a bottom, a left side, a right side, a U-shaped surface extending downwardly from said top in the middle area of said body and a surface which extends to said outer end surface and has a portion in the middle area of said body which curves outwardly and downwardly to said bottom, said bellows has a top, a bottom, a left side, a right side, and an expandable U-shaped surface extending downwardly from the top and including a bight portion which extends between said inner end surfaces of said head portion and said shoulder portion substantially linearly, and said head portion has a top, a bottom, a left side, a right side, an outer end, a U-shaped surface which extends downwardly from said top and outwardly from said head portion inner end surface and a contoured curved head receiving surface which extends outwardly from said U-shaped surface of said head portion and downwardly to said outer end and to said bottom of said head portion, all of said U-shaped surfaces in the middle, bight area of the U-shaped openings adapted to conform generally to the natural cervical curve of a patient's neck which is received therein.

4. The cervical traction device of claim 3 wherein said head receiving surface of said head portion extends downwardly to said bottom of said head portion within said head portion and said head portion at said bottom has a U-shaped notch extending inwardly from said outer end whereby a patient's head can rest partially on said head receiving surface and partially on a planar surface upon which said body of said cervical traction device is positioned.

5. The cervical traction device of claim 3 wherein said head portion has a shoulder between the generally U-shaped surface and said head receiving surface in the area on each side of said U-shaped space above said bight portion and below said top of said head portion for engaging and exerting pressure against the occipital bone on each side of a patient's head.

6. The cervical traction device of claim 3 wherein said contoured curved outer end surface of said shoulder portion extends inwardly from said sides of said shoulder portion and is inclined slightly inwardly toward said bellows for mating with the normal sloping of a patient's shoulders and said curved outer end surface of said shoulder portion has, on each side of the middle area of said shoulder portion on either side of said U-shaped space, a concave arcuate contour extending from said top toward said bottom of said shoulder portion to a position above said bottom and then generally downwardly to said bottom for being received over the left and right shoulders of a patient.

7. The cervical traction device of claim 3 wherein each sides of said head portion angles from said bellows inwardly of said head portion and toward the other side of said head portion.

8. The cervical traction device of claim 1 wherein said shoulder portion and said head portion are made of a foam material.

9. The cervical traction device of claim 1 wherein said bellows includes three undulating portions.

10. The cervical traction device of claim 9 wherein said undulating portions of said bellows extend above the adjacent U-shaped surfaces of said shoulder portion and said head portion.

11. The cervical traction device of claim 1 wherein said means for pumping air into and for pumping air out or relieving air from said bellows includes a conduit and a bulb air pump at the outer end of said conduit; said bulb air pump having a one way inlet valve at an outer end thereof and, at an inner end thereof, a manually operated relief valve.

12. The cervical traction device of claim 1 wherein said means for pumping air into or out of said bellows includes an electrically operated pump and a timer for controlling operation of said electrically operated pump whereby air can be intermittently pumped into and out of said bellows for treating muscle spasm in the neck or a herniated disk in the neck of a patient.

13. The cervical traction device of claim 1 further including a head strap, fastening means on each side of said head portion and attachment means on one side of said strap adjacent at least each end of said strap for coupling with said fastening means on each side of said head portion.

14. The cervical traction device of claim 1 wherein the width of said U-shaped openings in said shoulder portion, said bellows, and said neck portion is between approximately 4½ inches and 7 inches.

15. The cervical traction device of claim 14 wherein said width of said U-shaped openings is approximately 5½ inches.

16. The cervical traction device of claim 1 wherein the depth of said U-shaped openings in said shoulder portion and said head portion from the top of said body is between approximately 3 and 4 inches.

17. The cervical traction device of claim 16 wherein the depth of said U-shaped openings in said shoulder portion and said head portion is approximately 3½ inches.

18. A cervical traction device comprising: a body including a shoulder portion, a head portion and a bellows; said bellows, said shoulder portion and said head portion having aligned U-shaped openings therein adapted to receive a patient's neck; said shoulder portion having a top, a bottom, a left side, a right side, a U-shaped surface extending downwardly from said top in the middle area of said body and a surface which extends to said outer end surface and having a portion in the middle area of said body which curves outwardly and downwardly to said bottom; said bellows having a top, a bottom, a left side, a right side, and an expandable U-shaped surface extending downwardly from the top and including a bight portion which extends between said inner end surfaces of said head portion and said shoulder portion substantially linearly and said head portion having a top, a bottom, a left side, a right side, an outer end, a U-shaped surface which extends downwardly from said top and outwardly from said head portion inner end surface and a contoured curved head receiving surface which extends outwardly from said U-shaped surface of said head portion and downwardly to said outer end and to said bottom of said head portion; all of said U-shaped surfaces in the middle, bight area of said body adapted to conform generally to the natural cervical curve of a patient's neck which is received therein; and, means, connected to said bellows, for pumping air into said bellows and for relieving or pumping air out of said bellows.

19. A cervical traction device comprising: a body including a shoulder portion, a head portion and a bellows; said bellows, said shoulder portion and said head portion having aligned U-shaped openings therein adapted to receive a patient's neck; said head portion having a top, a bottom, a left side, a right side, an outer end, a U-shaped surface which extends downwardly from said top and outwardly from said head portion inner end surface and a contoured curved head receiving surface which extends outwardly from said U-shaped surface of said head portion and downwardly to said outer end and to said bottom of said head portion; said head portion having a shoulder between the generally U-shaped surface and said head receiving surface in the area on each side of said U-shaped space above said bight portion and below said top of said head portion for engaging and exerting pressure against the occipital bone on each side of a patient's head; and, means, connected to said bellows, for pumping air into said bellows and for relieving or pumping air out of said bellows.

20. The cervical traction device of claim 19 wherein said U-shaped surface of said head portion inclines slightly outwardly and rearwardly from said bellows.

21. The cervical traction device of claim 19 wherein said U-shaped surface and said contoured head receiving surface of said head portion incline outwardly to said sides of said head portion and rearwardly from said bellows.

22. The cervical traction device of claim 19 wherein said shoulder is located approximately 0.75 to 1.0 inch from said inner end surface of said head portion.

23. A cervical traction device comprising: a body including a shoulder portion, a head portion and a bellows situated between said shoulder portion and said head portion; said bellows, said shoulder portion and said head portion having aligned U-shaped openings therein adapted to receive a patient's neck; said shoulder portion having an outer end surface specially contoured to seat over the top center and front chest portions of the left and right shoulders of a patient and bear against said left and right shoulders when the bellows is inflated; and, means, connected to said bellows, for pumping air into said bellows and for relieving or pumping air out of said bellows thereby to extend the distance between said shoulder portion and said head portion.

24. The cervical traction device of claim 23 wherein the longitudinal extent of said U-shaped surface of said shoulder portion can extend between approximately 1 inch to approximately 2 inches.

25. A cervical traction device comprising: a body including a shoulder portion, a head portion and a bellows situated between said shoulder portion and said head portion; said bellows, said shoulder portion and said head portion having aligned U-shaped openings therein adapted to receive a patient's neck; a head strap; fastening means on each side of said head portion; attachment means on one side of said strap adjacent at least each end of said strap for coupling with said fastening means on each side of said head portion; and, means, connected to said bellows, for pumping air into said bellows and for relieving or pumping air out of said bellows thereby to extend the distance between said shoulder portion and said head portion.

26. The cervical traction device of claim 25 wherein said fastening means is located on said sides of said head portion adjacent said bottom of said head portion.

27. The cervical traction device of claim 25 wherein said fastening means includes a hook and loop fastening means.

28. A cervical traction device comprising: a body including a shoulder portion, a head portion and a bellows situated between said shoulder portion and said head portion; said bellows, said shoulder portion and said head portion having aligned U-shaped openings therein adapted to receive a patient's neck; means, connected to said bellows, for pumping air into said bellows and for relieving or pumping air out of said bellows thereby to extend the distance between said shoulder portion and said head portion; and, said means for pumping air into or out of said bellows includes an electrically operated pump and a timer for controlling operation of said electrically operated pump whereby air can be intermittently pumped into and out of said bellows for treating muscle spasm in the neck or a herniated disk in the neck of a patient.

* * * * *